United States Patent [19]

Schellenberger

[11] Patent Number: 6,001,586
[45] Date of Patent: Dec. 14, 1999

[54] COMPARTMENTALIZATION METHOD FOR SCREENING MICROORGANISMS

[75] Inventor: Volker Schellenberger, Burlingame, Calif.

[73] Assignee: Genencor International, Inc., Rochester, N.Y.

[21] Appl. No.: 08/625,488

[22] Filed: Mar. 29, 1996

[51] Int. Cl.⁶ .............................. C12Q 1/04; C12Q 1/02; C12Q 1/54

[52] U.S. Cl. ................................ 435/34; 435/29; 435/14; 435/15; 435/25; 435/23; 435/24; 435/28; 435/299.2; 435/300.1; 435/304.2

[58] Field of Search ................................ 435/34, 29, 14, 435/15, 25, 23, 24, 28, 19, 299, 300, 299.2, 300.1, 304.2

[56] References Cited

U.S. PATENT DOCUMENTS

| | | | |
|---|---|---|---|
| Re. 34,606 | 5/1994 | Estell et al. ............................. | 435/34 |
| 5,480,805 | 1/1996 | Wolf et al. ............................. | 435/34 |

OTHER PUBLICATIONS

Joyce, "Directed Molecular Evolution," *Scientific American*, Dec. 1992, pp. 90–97.
Joyce, "Evolution of Catalytic Function," *Pure&Appl. chem.*, 65(6):1205–1212, 1993.
Moore et al. "Directed Evolution of a Para–Nitrobenzyl Esterase for Aqueous–Organic Solvents," *Nature Biotechnology*, 14:458–467, Apr. 1996.
Osuna et al. "Microbial Systems and Directed Evolution of Protein Activities," *Critical Reviews in Microbiology*, 20(2):107–116, 1994.

*Primary Examiner*—Louise Leary
*Attorney, Agent, or Firm*—Christopher L. Stone

[57] ABSTRACT

A method is provided for screening microorganisms having a selectable characteristic comprising: (a) providing a growth chamber capable of forming a plurality of discrete compartments, said compartments comprising a barrier which inhibits the diffusion of metabolites or nutrients between said compartments within said growth chamber; (b) preparing a growth medium which, by its lack of or addition of one or more metabolites or nutrients, preferentially facilitates growth of microorganisms exhibiting said selectable characteristic from microorganisms which do not exhibit said selectable characteristic; (c) inoculating said growth medium with a plurality of microorganisms, a portion of which comprise said selectable characteristic; (d) placing said inoculated growth medium into said growth chamber so as to randomly disperse said microorganisms among discrete compartments in said growth chamber; and (e) incubating said growth chamber for a suitable time and under suitable conditions to obtain a detectable disparity of growth between microorganisms having said selectable characteristic and microorganisms lacking said selectable characteristic.

19 Claims, 3 Drawing Sheets

COMPARTMENTALIZATION METHOD FOR SCREENING MICROORGANISMS

BACKGROUND OF THE INVENTION

1. Field of the Invention

The present invention is directed to improvements in screening methods used to detect, amplify and select microorganisms subjected to mutagenesis which thereby develop desirable characteristics differing from the microorganisms prior to mutagenesis. More particularly, the present invention is directed to novel screening methods which enhance the growth of certain desired mutants in a pool of organisms which has been subjected to random mutagenesis in such a manner to permit screening of a large number of potential mutants efficiently and effectively.

2. State of the Art

In the prior art, several methods of directing the evolution of a pool of microorganisms subjected to random mutagenesis have been developed. One manner of effecting focused evolution of an organism is to introduce novel characteristics into protein products by site-directed mutagenesis. However, such methods require a high level of knowledge regarding the subject protein in terms of structure and function relationships and the specific effects desired. As a result, methods have been developed which take advantage of random mutational events over a large cell population and/or over several generations to produce a small number of desired mutations. Such methods, generally referred to as directed evolution, require the steps of obtaining a pool of starting material microorganisms, subjecting these microorganisms to random mutagenesis and subsequently applying appropriate selection techniques to select mutants having desired characteristics.

Essential to the success of directed evolution techniques are screening or selection techniques for isolating desired mutants. A common selection technique involves growing the mutant organisms under conditions such that only desired mutants exhibit growth. One such technique is to plate the mutant organisms on media which limits growth to microorganisms having a specific (mutant) characteristic. For example, media which includes a toxin will force selection of organisms having resistance to the toxin. Similarly, media which includes a substrate for which it is necessary that the mutant organisms be able to metabolize that substrate for survival will limit growth to those organisms capable of producing the appropriate enzymes. Further, the mutant organisms can be subjected to rigorous conditions to determine if, for example, the mutant organisms are better suited for surviving at high temperature or pH.

An example of such selection pressure is illustrated in Forney et al., Appl. Environ. Microb., vol. 55, no. 10, pp. 2550–2555 (1989), wherein mutant penicillin amidases with novel substrate specificity were obtained by mutagenizing a strain of E.coli and selecting on the ability of the mutants to hydrolyze glutaryl-(L)-leucine and provide leucine to Leu⁻ strains. Cells which retained the wild type enzyme would not grow on the minimal media containing glutaryl-(L)-leucine as the sole source of leucine. The authors reported that the growth rates of the Leu⁻ cells that expressed mutant amidases increased as the glutaryl-(L)-leucine concentration increased or as the medium pH decreased. As a result, it was possible for the authors to deliberately modify the substrate specificity of penicillin amidase and select mutants with amidases that were progressively more efficient at hydrolyzing glutaryl-(L)-leucine.

An alternative technique which was developed to screen mutant proteins is known as phage display. This technique is valuable in isolating randomly mutagenized DNA encoding proteins having a specific desired binding activity. In the phage display technique, a lambda phage or equivalent is produced which contains a mutagenized gene encoding a specific binding protein. The phage is then subjected to a ligand binding procedure, e.g., column affinity purification, wherein the ligand is selected based on a desired binding capability of the mutant binding protein and can thus selectively bind to and trap phage displaying the desired mutant binding protein on its surface. Subsequent to isolation, the trapped phage can be used to infect appropriate bacterial hosts to produce larger quantities of protein. One example of phage display is application as a tool for isolating proteases having new protease specificities, Corey et al., Gene, vol. 128, pp. 129–134 (1993), wherein phage display was utilized to identify mutant trypsin molecules which comprised a fusion product of the trypsin molecule and M13 coat proteins through capture by immobilized ecotin as a ligand.

The above methods have provided powerful mechanisms for applying selection pressure to effect isolation of specific desired mutants among a randomly mutagenized population. However, a problem remains in screening large numbers of organisms in an efficient manner. For example, plate screening requires serial dilutions of liquid cultures to the extent that only a small number of colonies exist on each plate. Where the mutant pool comprises millions of organisms, this imposes an enormous procedural burden on the researcher to analyze the entire population.

This problem is amplified where less stringent selection criteria are used to detect certain types of mutations, for example, improved catalytic activity, temperature or pH resistance in an enzyme. One example of such a selection technique involves use of media which includes a necessary cellular nutrient, access to which requires a specific mutation in an enzyme. In such instances, it is often advantageous to repeatedly mutate a population of microorganisms, screening between each mutational event to select for incrementally improved mutants. Because the mutants will have varying degrees of viability on the media as opposed to absolute viability or not, it becomes necessary to screen a much larger quantity of organisms thus adding to the procedural burden on the researcher.

Moreover, if the selection procedure involves the production of a necessary nutrient by a mutant extracellular enzyme, organisms lacking the necessary mutation will benefit from the production of mutant enzymes by other colonies due to nutrient diffusion through the media. Thus, it is necessary to drastically limit the number of colonies on a media plate through serial dilutions, while at the same time observing a large increase in the number of mutants analyzed. The combination of these effects means that on the order of 50–100 colonies per plate becomes a maximum. Due to these effects, plus the additive effect of mutagenizing over several generations, the burden becomes prohibitive if entire populations of microorganisms are to be screened. To avoid such burdensome screening, many researchers opt to analyze only a minor segment of the entire population, thus reducing the potential for detecting desired mutants.

From the above, it is apparent that advances have been made in the development of screening techniques for accurately identifying and isolating desired characteristics in proteins produced from randomly mutagenized genes. However, a problem remains in the art related to the large scale screening of mutants, particularly in the field of improved mutant of extracellularly produced enzymes. Given the miniscule proportion of desired mutant organisms produced during random mutagenesis in comparison with the total pool of microorganisms, it would be advantageous to find an accurate technique for the large scale screening and isolation of mutant organisms subsequent to random mutagenesis. Thus, a system which allows simple, speedy, accurate and efficient isolation of mutant organisms from a mutagenized pool on the order of 10,000 to 1,000,000 organisms without crossover of nutrients would greatly improve present techniques. The prior art, however, fails to provide such a system.

SUMMARY OF THE INVENTION

It is an object of the invention to provide for an efficient and accurate means to analyze large populations of mutant organisms.

It is another object of the invention to provide for a means which allows for an efficient means of subjecting successive generations to mutagenesis while simultaneously screening out undesired mutants.

It is another object of the invention to facilitate the screening of large populations of mutagenized organisms in and efficient and simple manner.

It is yet another object of the invention to provide for a system of easily analyzing and screening among a large number of mutants in sensitive selection systems.

It is yet another object of the invention to provide for a system which allows for accurate screening of random mutations in large numbers of organisms producing extracellular enzymes.

According to the present invention a method of screening microorganisms having a selectable characteristic comprising: (a) providing a growth chamber capable of forming a plurality of discrete compartments, said compartments comprising a barrier which inhibits the diffusion of metabolites or nutrients between said compartments within said growth chamber; (b) preparing a growth medium which, by its lack of or addition of one or more metabolites or nutrients, preferentially facilitates growth of microorganisms exhibiting said selectable characteristic from microorganisms which do not exhibit said selectable characteristic; (c) inoculating said growth medium with a plurality of microorganisms, a portion of which comprise said selectable characteristic; (d) placing said inoculated growth medium into said growth chamber so as to randomly disperse said microorganisms among discrete compartments in said growth chamber; and (e) incubating said growth chamber for a suitable time and under suitable conditions to obtain a detectable disparity of growth between microorganisms having said selectable characteristic and microorganisms lacking said selectable characteristic.

The invention itself, together with further objects and attendant advantages, will best be understood by reference to the following detailed description taken in conjunction with the accompanying drawings.

DETAILED DESCRIPTION OF THE INVENTION

"Selectable characteristic" means an identifiable characteristic of a microorganism which can be used as the basis for screening a specific microorganism or group of microorganisms from a larger pool which includes microorganisms which do not exhibit the selectable characteristic. For example, it is well known to use such selectable characteristics as antibiotic resistance, a necessary enzymatic activity for production of a nutrient or other compound necessary for cell growth or division. However, any characteristic which is capable of providing a basis for differentiating between a mutant organism and a non-mutant precursor organism will be an acceptable selectable characteristic. In a preferred embodiment, the selectable characteristic is the ability of a microorganism to produce an enzyme exhibiting altered performance or stability characteristics. Such altered performance or stability characteristics may comprise altered substrate specificity, altered specific activity, altered temperature/activity profile, altered salt or ion requirement or any combination of these characteristics. The specific enzyme subjected to the method of the invention may be any hydrolase, oxidoreductase, transferase, lyase or ligase. Preferably, the enzyme comprises a protease, a lipase, an amylase, a galactosidase, a cellulase, a lactase, a polygalacturonase, a glucoamylase, an esterase, a hemicellulase, a peroxidase, an oxidase, a laccase, a glucose oxidase, a ligninase, an NADH reductase or a 2,5 DKG reductase.

"Growth chamber" means a vessel or environment which is capable of supporting the growth or maintenance of microorganisms. Thus, test tubes, well plates, shake flasks and any other well known culturing vessel is considered a growth chamber. For the purposes of the present invention, a growth chamber is capable of forming a plurality of discrete compartments, each compartment capable of maintaining or allowing the growth of microorganisms. The discrete compartments, or compartments, should be of such a nature to minimize diffusion of nutrients or cell products between two or more compartments.

Any system of preparing discrete compartments which allows preparation of small discrete pools or drops of media that allow minimal or no inter-pool diffusion of media components such as metabolites or nutrients will suffice as a growth chamber. Critical for the present invention is that each discrete compartment be separated by a barrier to the diffusion of metabolites or nutrients and enzymes; the barrier being composed of any combination of air, a solid material and/or a liquid. Preferably, the growth chamber will facilitate the development of at least about 5,000 compartments. More preferably, the growth chamber will facilitate the development of at least about 50,000 compartments, and most preferably greater than about 100,000 compartments. While there is no upper limit necessary for the number of compartments, a preferred growth chamber should hold less than about 1,000,000 compartments to permit ease of analysis. The size of the compartments will generally not be greater than 1 ml. Preferably, the compartment size is between about 0.005 μl and about 50.0 μl, more preferably between about 0.01 μl and about 10.0 μl, and most preferably between about 0.05 μl and about 1.0 μl. The concentration of microorganisms in the media should be such that, upon random dispersion of the pool of mutant microorganisms throughout the growth chamber, at least 25% of the compartments contain only one microorganism. Preferably, at least 50% of the compartments contain only one organisms and more preferably at least 75% of the compartments contain only one microorganism. In a most preferred embodiment, the concentration of microorganisms upon random dispersion is such that only one microorganism is present in any one compartment.

Specific examples of suitable growth chambers according to the present invention include: a column filled with inert carrier beads (i.e., glass or polymer based beads) which trap "pools" of inoculated media at the surface contact points between the beads; the use of a bundle or plurality of hollow tubes which are capable of supporting small amounts of inoculated media separated by air as discrete compartments; dispersion of the inoculated growth medium in a non-miscible fluid so as to form discrete drops of inoculated medium throughout the non-miscible fluid, preferably then solidifying the non-miscible fluid to prevent exchange of nutrients or cell products between droplets of media; encapsulation of medium in wax or other substances capable of solidifying to form a matrix or barrier impermeable to mingling of certain nutrients between droplets or compartments of inoculated media; or liposomes.

A preferred method of producing a growth chamber using beads comprises filling a column with beads and allowing a small amount of inoculated medium to penetrate the bead matrices completely, preferably under vacuum. The dilution of the inoculum should be such that a significant proportion of the discrete media droplets trapped at the contact points of the beads will contain only one microorganism. Generally, the beads may be made of any suitably microbially inert substance, such as acrylic, silanized glass, resin, nylon, polypropylene, polyethylene, polystyrene, teflon or any other art recognized substance having similarly microbially inert properties. Preferably glass or acrylic beads are used, most preferably silanized glass. The beads may be of any size which is suitable for the formation of contacts between the beads to trap media. Preferably the size of the beads is from 0.25 mm to 5 mm preferably from 0.75 mm to 3.0 mm and most preferably from 1.0 mm to 2.0 mm. In this manner, it is possible to form a column having in the range of from 10,000 to 100,000,000 pools per liter of column volume. More preferably, between 100,000 and 5,000,000 pools are trapped per liter of column volume and most preferably between 250,000 and 1,000,000 pools are trapped per liter of column volume.

In yet another preferred embodiment, a growth chamber consists of a bundle of hollow fibers having porous or non-porous walls. For example, common oxygenators are suitable for such purposes. In one variation of this embodiment, the oxygenator is filled with inoculated media. The fibers are surrounded by air which blocks diffusion of most compounds between the individual fibers. The inoculation density of the medium in chosen such that cells are far apart within the fibers in order to reduce or prevent diffusion. Diffusion of metabolites or enzymes within the fibers can be further reduced by increasing the viscosity of the medium. By way of example, a single fiber of about six inches may have from 10–40 individual media "compartments". When using a hollow tube arrangement, preferably the tubes have a diameter of from about 0.05 to about 3 mm more preferably from about 0.1 to about 0.5, and most preferably from about 0.2 to about 0.3. In a preferred embodiment, using a viscous media, such as MOPS, the concentration of the organisms is such that they are about 10 mm apart in the fibers, thus allowing in general about 1–3 days before essential nutrients will diffuse the full 10 mm distance.

"Growth medium" means any combination of nutrients, salts, buffers, and other components recognized as beneficial to the growth of the specific microorganism being subjected to directed evolution. However, where screening is based on the development of a selectable characteristic involving the ability to process a nutrient or to be resistant to a specific compound, the growth medium should reflect that strategy by either lacking or having added thereto the specific compound which enables selection based on the selectable characteristic. Thus, where the selectable characteristic involves the production of a mutant protease which has the ability to act under certain temperature or environmental conditions, the growth media may include a nitrogen source which requires proteolytic activity for access by the microorganism. In this manner, microorganisms which do not have the appropriate proteolytic activity after mutation will not grow due to the lack of an available nitrogen source.

"Mutational event" means any method for inducing the mutation of DNA in an organism. Art recognized means of effecting mutations in DNA such as exposure to x-ray, gamma-ray, ultraviolet light, chemical mutagens such as ethyl methylsulfonate N-methyl-N'-nitro-N-nitroso guanidine are all acceptable means for the present invention of producing a mutational event. Mutations may also be introduced using enzymatic methods such as PCR or by transformation of the DNA into organisms which possess a high mutation frequency and subsequent extraction of the DNA.

The generalized design of an enrichment-based selection system such as described herein in practice calls for multiple rounds of selection: after cells have grown to an optimal density—the density at which the faster-growing variant is most enriched with respect to the population—the cells are removed from the growth chamber and a random sample is diluted, optionally mutagenized again, and introduced into a growth chamber for another round of enrichment. After a number of rounds, a consistently fast grower with respect to the population should be significantly enriched. The stringency of the selection criteria will depend on the characteristic selected for. For example, where it is merely required that an enzyme producing microorganism out-compete a non-enzyme producing microorganism, significant selection may be obtained in only one round. With respect to other characteristics, however, it may be necessary to use multiple rounds of selection. In such circumstances, it will be advantageous to utilize a growth chamber which has a relatively large number of compartments to facilitate screening a large number of organisms.

In a preferred embodiment of the present invention, the method of screening microorganisms having a selectable characteristic is used to differentiate mutant organisms having a specific selectable characteristic from mutant and/or non-mutant organisms which do not exhibit the specific selectable characteristic. Thus, the method of the invention requires that a growth chamber be provided which is capable of forming a plurality of discrete compartments. The compartments will comprise a barrier which inhibits the diffusion of metabolites or nutrients between the compartments within the growth chamber which barrier can be of a solid, liquid or gaseous nature. The compartments then separate a growth medium which contains a pool of mutagenized microorganisms. In practice, the growth medium may be inoculated with already mutagenized microorganisms prior to placing into the growth chamber, or organisms may be placed in the growth chamber and subsequently subjected to a mutational event. In either case, the growth medium, by its lack of or addition of one or more metabolites or nutrients, preferentially facilitates growth of microorganisms exhibiting the selectable characteristic from microorganisms which do not exhibit the selectable characteristic.

The inoculated growth medium should be placed into the growth chamber so as to randomly disperse the microorganisms among the discrete compartments in the growth chamber. It is important that the dilution of microorganisms in the inoculated growth medium be monitored to ensure that the concentration is not so great to result in too many microorganisms being placed in compartments and also not too small so as to result in inefficient screening. In any event, upon random dispersion of the microorganisms among the various compartments in the growth chamber, a significant portion, i.e., at least 25%, of the compartments should contain only one organism. When randomly dispersed in this way, each microorganism, after incubating for a suitable time and under suitable conditions, will grow only in response to its ability to exhibit the selectable characteristic. Incubation conditions will vary depending on the specific microorganism being grown, the effect of the conditions on the detection of the selectable characteristic, the size of the compartment and other factors which will be easily ascertained in accordance with routine practices.

Microorganisms which do not exhibit the selectable characteristic will suffer a detectable lack of growth compared to microorganisms having the selectable characteristic. This disparity of growth will ensure that when the microorganisms are taken from the compartments, the portion of microorganisms which exhibit the selectable characteristic are significantly enriched in the total population. In a preferred embodiment, the contents of the compartments are combined and the resulting pool analyzed for the ability to exhibit the selectable characteristic. It will often be advantageous to subject the population again to mutagenesis and screening as described herein to even more significantly enhance the proportion of microorganisms in the pool which have the selectable characteristic.

By following the teachings of the invention, it is possible to greatly improve the efficiency by which the evolution of a specific microorganism may be directed to a desired end. To illustrate the surprising results achieved by Applicants herein and which are achievable by practicing the herein disclosed invention, the following non-limitative examples are provided.

EXAMPLES

Example 1

Compartmentalization Using Glass Balls—Diffusion Study

Glass balls of various sizes ranging from 30 microns to 2 millimeters were obtained from Jaygo, Inc. (NJ). 1/8 inch nylon, polypropylene, polyethylene, and polystyrene balls were obtained from United States Plastic Co. (Lima, Ohio). 1/8" teflon balls were obtained from Cole-Parmer (Niles, Ill.). 1/16" acrylic balls were obtained from Salem Specialty Ball Co. (W. Simsbury, Conn.) and 1/16" teflon balls were obtained from Bal-Tec, Inc. (Los Angeles, Calif.).

Two milliliter glass columns were obtained from Bio-Rad (cat# 737-0706, Hercules, Calif.). 1.25 milliliter plastic Bio-Spin columns were obtained from Bio-Rad (cat# 732-6008).

Growth medium employed was Spizizen's Minimal Medium (SMM) at half strength (0.5×SMM) with 2.5 grams/liter of bovine serum albumin (BSA) (Sigma, St. Louis, Mo.) as the sole added nitrogen source:

75x SMM Stock (per liter):

70 g $K_2HPO_4$
30 g $KH_2PO_4$
5 g $Na_3$ Citrate • $2H_2O$
1 g $MgSO_4$
100x Micronutrients (per 50 ml)

20 ml 1 g/l $FeSO_4$
5 ml 1 g/l $MnCl_2$ • 2 $H_2O$
5 ml 1 g/l $ZnSO_4$ • 7 $H_2O$
5 ml 0.5 g/l $CuCl_2$ • 2 $H_2O$
5 ml 1 g/l $CoCl_2$ • 6 $H_2O$
5 ml 1 g/l $NaMoO_4$ • 2 $H_2O$
5 ml 1 g/l $Na_2B_4O_7$ • 10 $H_2O$
0.5X SMM + 2.5 g/l BSA (per liter):

200 ml 5x SMM
10 ml 1M $NH_4Cl$
1 ml 0.1M $CaCl_2$
10 ml 100x Micronutrients
14 ml 50% Glucose
100 ml 25 g/l BSA
500 ul 10 mg/ml Chloramphenicol
Resultant pH = 7.4

To study the effect of diffusion in the glass ball system, glass balls of various sizes were washed with RBS-pF detergent (Pierce, Rockford, Ill.), rinsed exhaustively and dried in an oven at 92° C. The balls were transferred into 1.25 ml semi-transparent plastic columns to a millimeter below the top of the column bed. The columns were placed on a vacuum manifold, the growth medium was applied to the top of the column, and the vacuum was applied for varying lengths of time to remove the bulk of the medium. A filter obtained from the bottom of an unused plastic column was then placed on the top of the balls and 3 microliters of a 50 mg/ml aqueous solution of chlorophenol red was applied to the filter with a syringe. The columns were sealed and incubated at 37° C. The distance travelled by the purple dye in a given time period was recorded and accepted as a measure of the rate of diffusion in the system.

Diffusion in a system of 1/8" balls of various materials was performed similarly except that the balls were placed into 2 ml glass columns, the dye was delivered to the middle of the bead matrix and diffusion was determined qualitatively by macro- and microscopic observation.

Figure 1:
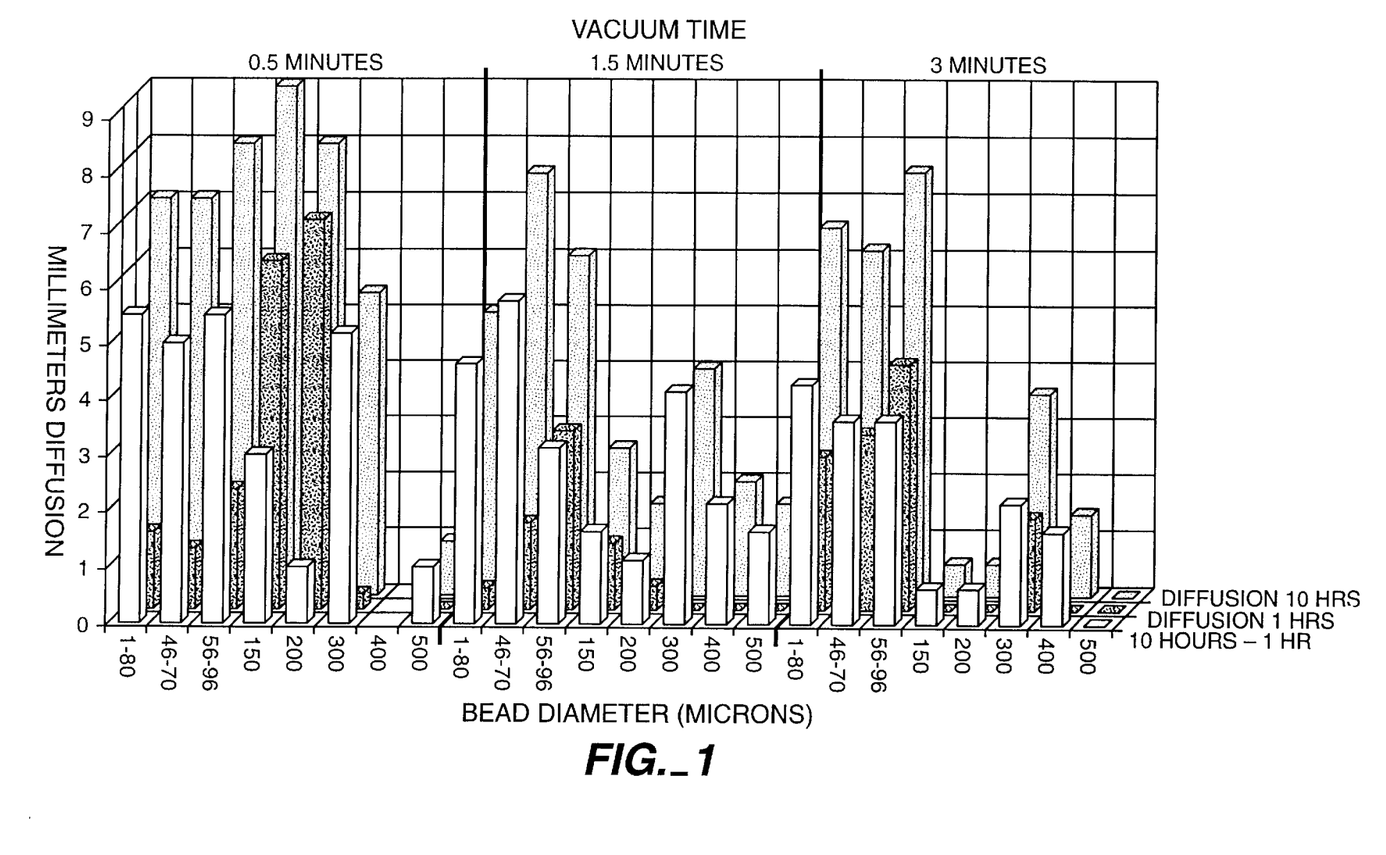
FIG. 1 illustrates the results of experiments detecting the optimum relationship between diffusion and bead size according to a preferred embodiment of the invention.

The diffusion of nutrients (exemplified by the dye diffusion) through the system was studied in columns of glass balls ranging in mean diameter from 30 microns to 500 microns. Medium was removed from the columns by applied vacuum periods of 0.5, 1 and 1.5 minutes. Diffusion as indicated by the vertical distance travelled by chlorophenol red dye was most significant for ball sizes up to 95 microns but decreased significantly for 150 and 200 micron balls. Interestingly, diffusion again increased for 300 micron balls then decreased again for 400 and 500 micron balls. As shown in FIG. 1, the diffusion pattern exhibited a double peak when plotted versus mean ball diameter for all three vacuum times.

1/8" inch diam. balls of glass, nylon, polyethylene, polystyrene, acrylic, silanized glass, polypropylene and teflon were loaded into 2 ml glass columns and diffusion was similarly studied except that dye was injected in the middle of the ball matrix and quantitative observations were made by viewing under a dissecting microscope.

The desired behavior of the medium is to form micropools of uniform size only at ball contacts. When larger pools form over the surface of several balls ("pooling") the size distribution is greater and the system is more difficult to control: some cells may be trapped in small pools and others in larger pools, which may bias growth. Similarly, tiny beadlets on the surface of balls away from the contacts ("beading") leads to a greater size distribution. A summary of the observations are provided in Table 1.

TABLE 1

| Material | Diffusion | Pooling | Beading | Crit. Surface Tension |
|---|---|---|---|---|
| Glass | +++ | ++ | − | 47 |
| Nylon | +++ | ++ | − | 46 |
| Polyethylene | ++ | ++ | − | (33) |
| Polystyrene | + | ++ | + | N.F. |
| Acrylic | − | − | − | N.F. |
| Silanized Glass | − | ++ | + | N.A. |
| Polypropylene | − | ++ | +++ | 31 |
| Teflon | − | + | + | 18.5 |

+++ = Very significant,
++ = significant,
+ = marginally significant,
− = not observed
N.F. = Not found in the literature,
N.A. = not available Polyethylene used was linear polyethylene. Critical surface tension reported for polyethylene, however, was taken from a reference that does not indicate the type. The primary silane component of the siliconizing reagent, Aquasil (Pierce, Rockford, Ill.), is an octadecyltrialkoxysilane $CH_3(CH_2)_{16}CH_2Si(OR)_3$ and because of its hydrophobicity can be reasonably expected to have a low critical surface tension, providing it completely covers the glass ball surface.

Diffusion was related to the critical surface tension of the ball material. The critical surface tension of a material is defined as the surface tension of a liquid below which the surface of the material becomes wet. Those materials with very low critical surface tensions (e.g. teflon, polypropylene, silanized glass) were effective in completely isolating medium in small droplets, completely preventing diffusion. These hydrophobic materials, however, also tended to exhibit greater beading. Of the materials tested, acrylic showed the most ideal properties: medium was confined to ball contacts with no significant diffusion, pooling or beading.

Example 2

Selection Experiments Using Glass Beads 2 mm glass balls were washed with RBS-pF detergent, rinsed exhaustively and dried in an oven at 92° C. The balls were transferred into 2 ml glass columns to the top of the column bed and the columns were placed on a vacuum manifold. 1.5 ml of Aquasil siliconizing solution (Pierce, Rockford, Ill.) was applied to the columns and allowed to penetrate the bead matrices completely. When necessary, bubbles were removed by tapping the glass with a metal rod. After 1 hour, the fluid was drained from the columns by opening the stopcocks on the vacuum manifold and applying approximately 20 mm Hg vacuum until the columns had completely dried (about 1 hour).

Two *Bacillus subtilis* strains were used to test the hypothesis that diffusion control can be used to select for strains having positive characteristics over other negative strains for a certain enzymatic activity. Both strains were deleted for their two major proteases. However, one of the strains was subsequently transformed with a plasmid carrying the gene for GG36 subtilisin from *Bacillus lentus*. The protease-producing strain ("positive" strain) and the control strain ("negative" strain) were each grown separately to log phase in 0.5×SMM with $NH_4Cl$ as the nitrogen source. Each culture was washed three times with nitrogen-free 0.5× SMM and resuspended in nitrogen-free 0.5×SMM. The strains were mixed in a ratio of 30:70 favoring non-protease producers over protease producers. The mixed inoculum was diluted and applied to a series of columns of glass balls. The remaining inoculum was placed into a 50 ml plastic conical tube and incubated at 37° C. on a rotary shaker at 300 rpms. Additionally, both strains were prepared at the approximate density expected in the columns when cells are in micropools of medium, and grown separately in tubes at 37° C. and 300 rpms.

One ml of the mixed inoculum was applied to the top of each column and allowed to penetrate the bed by opening the stopcocks on the vacuum manifold under gravity only. A slight vacuum approximately 200–700 mmHg was then applied to allow the bulk of the medium to drain from each column without leaving a foam, then full vacuum approximately 20 mmHg was applied for one minute. The objective here was to trap medium at ball contact points and to minimize the "pooling" of medium over the surface of multiple beads, without drying up medium at the top of the columns. The columns were then sealed and placed in a closed styrofoam container in a 37° C. incubator. It is estimated that the volume of the compartments formed at the contact surface of the beads averaged in the range of from 0.01 to 0.1 $\mu l$. Based on this volume and the concentration of organisms in the medium, it is estimated that each "compartment" contained on average 0.2–0.8 organisms.

Column Parameters

Fraction of glass in column=56%

Fraction of air in column=41.7% (no further aeration necessary)

Fraction of medium in column=2.3%

Number of pools per liter column volume=520,000 (estimated)

At appropriate time points, a column was removed from the incubator. The plug seals were removed, the bottom of the column was placed into a 15 ml plastic conical tube, 1 ml of 0.5×SMM+$NH_4Cl$ was added at the top of the column, and the column was spun in a swinging rotor bucket for approximately one minute, resulting in the collection of approx. 1 ml of medium in the 15 ml conical tube. 10-fold serial dilutions were made of the collected medium and plated onto agar medium containing 1.6% skim milk and incubated at 37° C. for approximately 15 hours. The number of colonies producing a clearing zone, indicating proteolysis of the skim milk substrate, was counted as well as the number without clearing zones.

Figure 2:
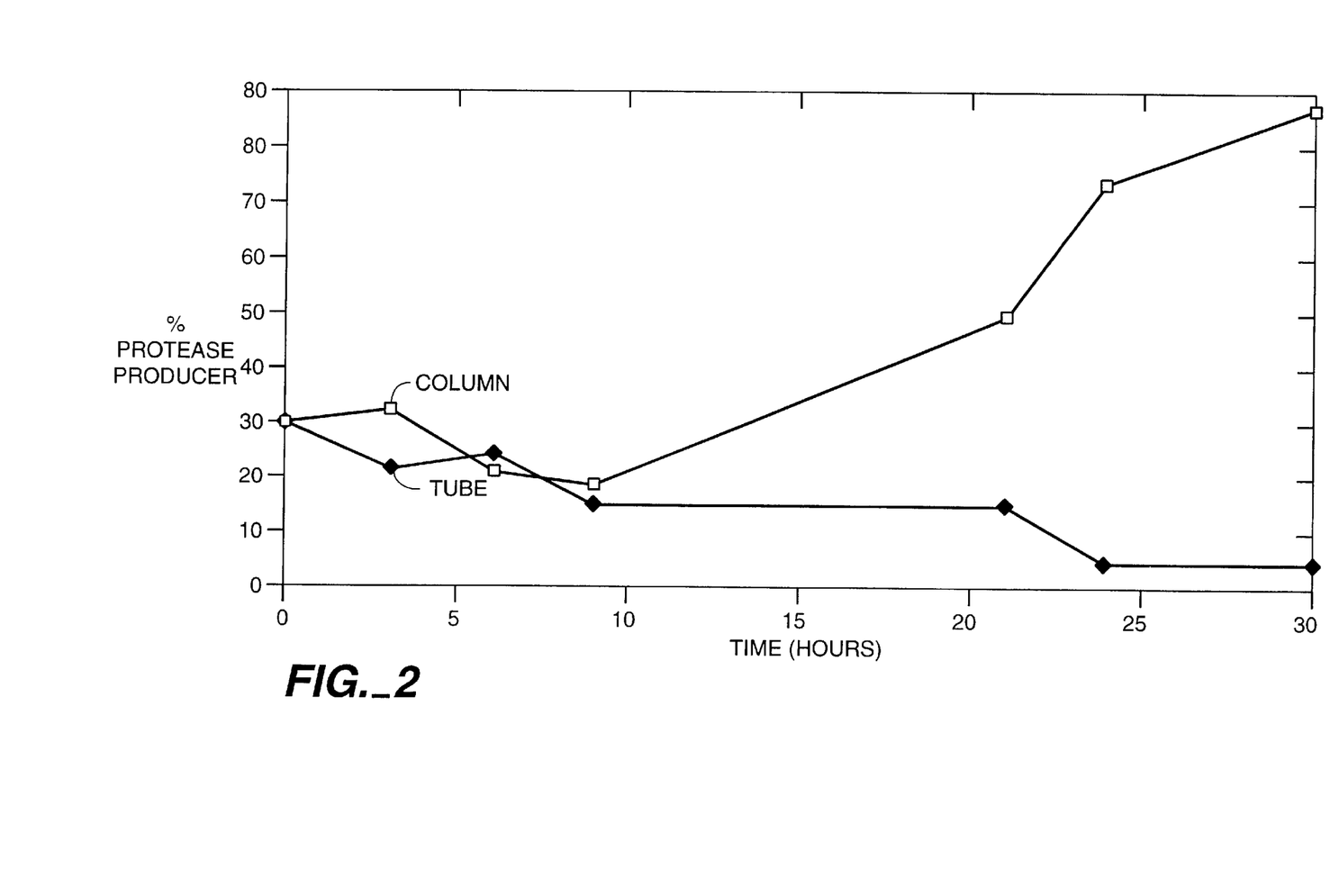
FIG. 2 illustrates the results of experiments showing the growth pattern of a population of microorganisms of which 20% exhibit protease production capability and 80% do not. In one example, the mixture of bacteria is subjected to the method of the invention comprising compartmentalizing the mixtures using glass beads. In the second example, the mixture of bacteria is incubated under identical conditions as the first example except that they are grown in a single test tube.

The relative percentage of protease producers to non-protease producers was determined at various times and is illustrated in FIG. 2.

As shown in FIG. 2, the percentage of the protease-positive strain in the columns decreased from the start of the experiment to 9 hours from 30% to 20%, and then steadily increased to approximately 90% at 30 hours. Thus the positive strain was significantly enriched in this system. The same inoculum when grown in a tube, however, favored growth of the protease-negative strain, as the percentage of positives decreased over time from 30% to 5% at 30 hours.

Example 3

Selection Experiment Using An Oxygenator

The two strains of *Bacillus subtilis* as described above in Example 1 were mixed in a ratio of 20:80 (protease positive:protease negative) in a MOPS 1A medium containing 2.5 g/l BSA, 100 μM $NH_4Cl$ and 3% (w/v) hydroxy-ethyl cellulose (Aldrich, Milwaukee, Wis.). The mixture was inoculated into 3 different Oxy-1 hollow fiber oxygenators (Unisyn Technologies, Inc. Hopkinton, Mass.) as well as in a test tube and incubated at 37° C. for varying lengths of time. The oxygenators had 1800 hollow fibers with an average fiber volume of 0.004 ml. Based on the concentration of the inoculum, an average number of 3–8 colonies per fiber was expected. The hollow fibers prevent the diffusion of nutrients or hydrolysis products laterally while the use of the viscous medium described above ensured that diffusion along the tube length was minimized.

Figure 3:
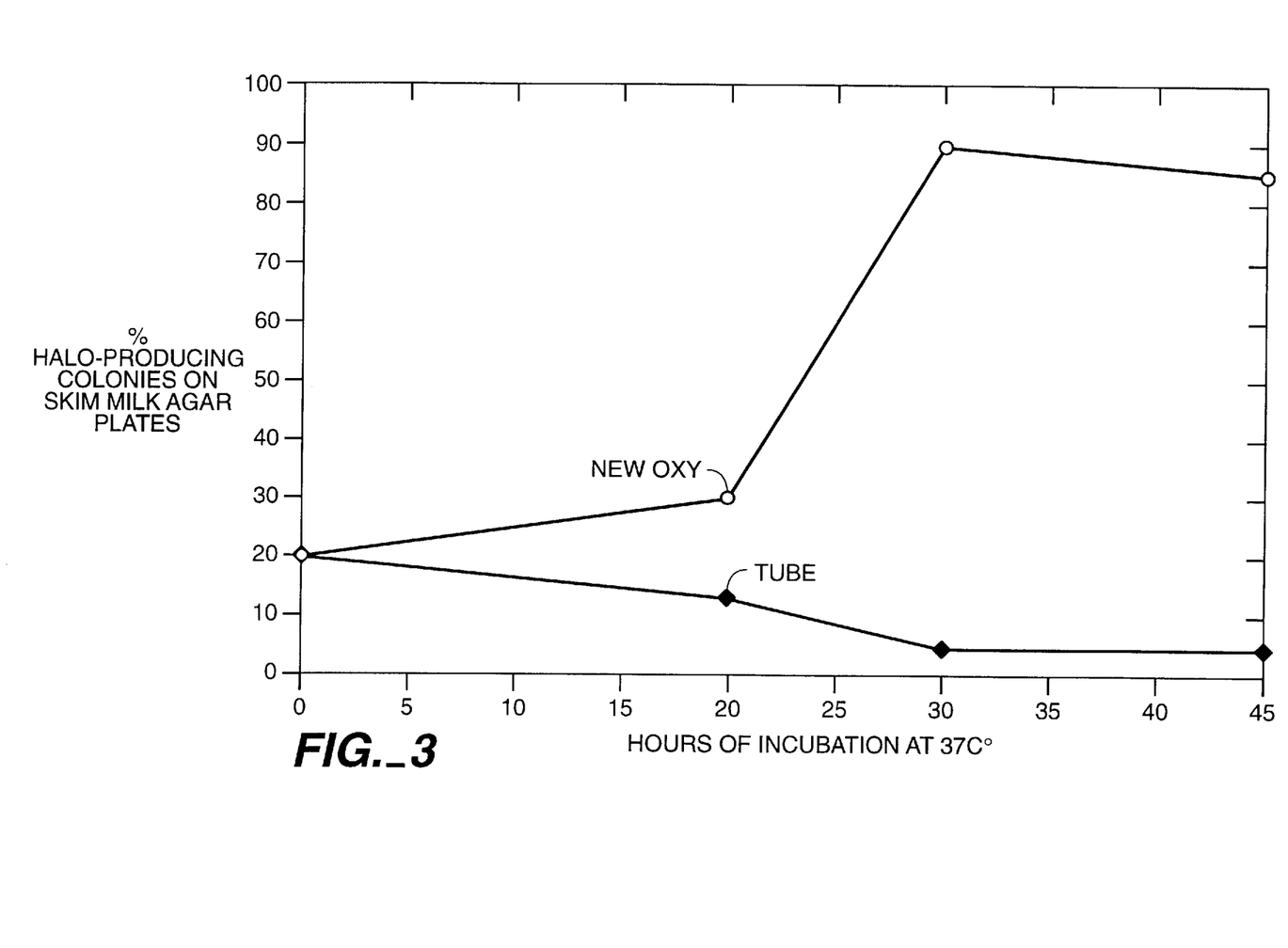
FIG. 3 illustrates the results of experiments showing the growth pattern of a population of microorganisms of which 20% exhibit protease production capability and 80% do not. In one example, the mixture of bacteria is subjected to the method of the invention comprising compartmentalizing the mixtures using an oxygenator or hollow fiber cartridge. In the second example, the mixture of bacteria is incubated under identical conditions as the first example except that they are grown in a single test tube.

The tube and oxygenators were placed on a rolling wheel to provide oxygenation. At 20, 30 and 45 hours an aliquot was removed from the tube and an oxygenator was removed from incubation. The medium was removed from the oxygenator and plated onto skim milk containing agar plates. As shown in FIG. 3, the percentage of colonies from the oxygenators and from tubes that produced clearing zones versus time was markedly different as incubation proceeded. For example, in a test tube, at 30–45 hours the percentage of protease producing colonies was around 5% whereas in the oxygenator the percentage of protease producing colonies was around 85–90%.

Of course, it should be understood that a wide range of changes and modifications can be made to the preferred embodiment described above. It is therefore intended that the foregoing detailed description be understood that it is the following claims, including all equivalents, which are intended to define the scope of this invention.

I claim:

1. A method of screening microorganisms having a selectable characteristic comprising:
   (a) providing a growth chamber capable of forming a plurality of discrete compartments, said compartments comprising a barrier which inhibits the diffusion of metabolites or nutrients between said compartments within said growth chamber and comprising hollow fibers, glass beads, a dispersion of the inoculated media in a non-miscible fluid, or encapsulated media in a solid matrix;
   (b) preparing a medium which, by its lack of or addition of one or more metabolites or nutrients, preferentially facilitates growth of microorganisms exhibiting said selectable characteristic from microorganisms which do not exhibit said selectable characteristic;
   (c) inoculating said medium with a plurality of microorganisms, a portion of which comprise said selectable characteristic;
   (d) placing said inoculated medium into said growth chamber so as to randomly disperse said microorganisms among discrete compartments in said growth chamber;
   (e) incubating said growth chamber for a suitable time and under suitable conditions to obtain a detectable disparity of growth between microorganisms having said selectable characteristic and microorganisms lacking said selectable characteristic; and
   (f) selecting microorganisms identified as having said selectable characteristic wherein said method results in a higher proportion of microorganisms exhibiting said selectable characteristic compared to an identical method of screening except for the absence of discrete compartments.

2. The method according to claim 1, wherein upon random dispersion, at least 25% of said discrete compartments contain only one microorganism.

3. The method according to claim 2, wherein 50% of said compartments contain only one microorganism.

4. The method according to claim 3, wherein 75% of said compartments contain only one microorganism.

5. The method according to claim 4, wherein substantially all of said compartments contain only one microorganism.

6. The method of claim 1, wherein said compartments comprise a volume of between about 0.1 and about one milliliter.

7. The method of claim 1, wherein said compartments comprise a volume of between about 0.001 and about 0.1 milliliter.

8. The method of claim 1, wherein said compartments comprise a volume of between about 0.0001 and about 0.01 milliliter.

9. The method of claim 1, wherein said selectable characteristic comprises a mutant enzyme exhibiting altered performance.

10. The method of claim 9, wherein said mutant enzyme exhibiting altered performance comprises characteristics selected from the group consisting of altered substrate specificity, altered specific activity, altered temperature/activity profile, altered pH/activity profile, altered salt or ion requirements, and altered activity or stability in the presence of surfactants, solvents, or other solutes.

11. The method of claim 9, wherein said enzyme comprises a hydrolase, an oxidoreductase, a transferase, a lyase or a ligase.

12. The method of claim 9, wherein said enzyme comprises a protease, lipase, amylase, β-galactosidase, cellulase, lactase, polygalacturonase, β-glucoamylase, esterase, hemicellulase, peroxidase, oxidase, laccase, glucose oxidase, ligninase NADH reductase or 2,5 DKG reductase.

13. The method of claim 1, wherein said microorganisms comprise bacteria, filamentous fungi or yeast.

14. The method of claim 1, wherein said microorgansims are subjected to mutagenesis prior to inoculating said growth medium with said microorganisms.

15. A method of isolating microorganisms having a selectable characteristic comprising:
   (a) preparing a population of microorganisms for which said selectable characteristic is desired and subjecting said population to one or more mutational events to produce mutant microorganisms;
   (b) providing a growth chamber capable of forming a plurality of discrete compartments, said compartments comprising a barrier which inhibits the diffusion of metabolites or nutrients or proteins between said compartments within said growth chamber;
   (c) preparing a growth medium which, by its lack of or addition of one or more metabolites or nutrients, preferentially facilitates growth of said mutant microorganisms exhibiting said selectable characteristic from mutant or non-mutant microorganisms which do not exhibit said selectable characteristic;
   (d) inoculating said growth medium with said mutant microorganisms;

(e) placing said inoculated growth medium into said growth chamber so as to randomly disperse said inoculated microorganisms among discrete compartments in said growth chamber;

(f) incubating said growth chamber for a suitable time and under suitable conditions to obtain a detectable disparity of growth between mutant microorganisms having said selectable characteristic and microorganisms lacking said selectable characteristic; and (g) selecting said mutant microorganisms identified as having said selectable characteristic.

16. The method according to claim 15, wherein said step (b) occurs prior to step (c).

17. The method according to claim 15, wherein said step (b) occurs simultaneously with or subsequent to step (c).

18. The method according to claim 15, wherein 50% of said compartments contain only one microorganism.

19. The method according to claim 18, wherein substantially all of said compartments contain only one microorganism.

* * * * *